US012692490B2

(12) United States Patent
Kuwano et al.

(10) Patent No.: US 12,692,490 B2
(45) Date of Patent: Jul. 28, 2026

(54) METHOD FOR PREPARING RNA DERIVED FROM SKIN SURFACE LIPIDS

(71) Applicant: KAO CORPORATION, Tokyo (JP)

(72) Inventors: Tetsuya Kuwano, Kawasaki (JP);
Takayoshi Inoue, Tokyo (JP)

(73) Assignee: KAO CORPORATION, Tokyo (JP)

( * ) Notice: Subject to any disclaimer, the term of this patent is extended or adjusted under 35 U.S.C. 154(b) by 911 days.

(21) Appl. No.: 17/910,755

(22) PCT Filed: Mar. 11, 2021

(86) PCT No.: PCT/JP2021/009780
§ 371 (c)(1),
(2) Date: Jan. 10, 2023

(87) PCT Pub. No.: WO2021/182568
PCT Pub. Date: Sep. 16, 2021

(65) Prior Publication Data
US 2023/0242898 A1 Aug. 3, 2023

(30) Foreign Application Priority Data
Mar. 11, 2020 (JP) ................................ 2020-041910

(51) Int. Cl.
*C12N 15/10* (2006.01)
(52) U.S. Cl.
CPC ..... *C12N 15/1017* (2013.01); *C12N 15/1006* (2013.01)
(58) Field of Classification Search
CPC ........................ C12N 15/1006; C12N 15/1017
See application file for complete search history.

(56) References Cited

U.S. PATENT DOCUMENTS

| | | | |
|---|---|---|---|
| 11,913,061 B2 * | 2/2024 | Inoue ..................... | C12N 15/09 |
| 2005/0123965 A1 | 6/2005 | Yamashita et al. | |
| 2008/0033161 A1 | 2/2008 | Kanehara | |
| 2009/0111114 A1 | 4/2009 | Yamashita et al. | |
| 2010/0063268 A1 | 3/2010 | Kanehara et al. | |
| 2013/0052721 A1 * | 2/2013 | Hollander .......... | C12N 15/1003 |
| | | | 435/270 |
| 2014/0113294 A1 | 4/2014 | Horton et al. | |
| 2014/0272993 A1 | 9/2014 | Van Keuren-Jensen et al. | |

| | | | |
|---|---|---|---|
| 2017/0166955 A1 | 6/2017 | Birnboim et al. | |
| 2017/0198279 A1 | 7/2017 | Loeper et al. | |
| 2018/0371524 A1 * | 12/2018 | Inoue ................... | C12Q 1/6886 |
| 2021/0204919 A1 | 7/2021 | Hershey et al. | |
| 2022/0002782 A1 * | 1/2022 | Inoue ................... | C12Q 1/6883 |
| 2023/0265515 A1 * | 8/2023 | Takada ............... | G01N 33/6893 |
| | | | 435/6.1 |
| 2024/0011093 A1 * | 1/2024 | Shima ................ | G01N 33/6863 |
| 2024/0117433 A1 * | 4/2024 | Inoue ................. | C12N 15/1093 |
| 2024/0173019 A1 | 5/2024 | Hershey et al. | |
| 2024/0263225 A1 * | 8/2024 | Ueda .................... | C12Q 1/6876 |
| 2024/0294902 A1 * | 9/2024 | Uehara ............. | C12N 15/1065 |
| 2024/0294966 A1 * | 9/2024 | Inoue ................... | C12Q 1/6806 |

FOREIGN PATENT DOCUMENTS

| | | |
|---|---|---|
| CN | 1637012 A | 7/2005 |
| CN | 106574265 A | 4/2017 |
| JP | 2007-117084 A | 5/2007 |
| JP | 2007-325562 A | 12/2007 |
| JP | 2017-508478 A | 3/2017 |
| JP | 2018-183156 A | 11/2018 |
| JP | 2020-508689 A | 3/2020 |
| KR | 20080031590 A | 4/2008 |
| WO | WO-00/09754 A2 | 2/2000 |
| WO | WO-2018/008319 A1 | 1/2018 |
| WO | WO-2018/161062 A1 | 9/2018 |

OTHER PUBLICATIONS

Inoue et al., "Non-invasive human skin transcriptome analysis using mRNA in skin surface lipids," Communications Biology, Mar. 9, 2022, 5(1):215, 1-13, with Supplementary Information, 10 pages.
Qiagen, "RNeasy Lipid Tissue Mini Handbook," Jul. 1, 2018, XP093137678, Retrieved from the Internet: URL:https://www.qiagen.com/us/resources/download.aspx?id=7f13ac1a-841d-4e9b-b39d-42fe71b3d585&lang=en [retrieved on Mar. 5, 2024], 44 pages.
Supplementary European Search Report dated Mar. 21, 2024 in EP 21767977.8.
International Search Report dated Apr. 13, 2021 issued in International Application No. PCT/JP2021/009780, with English translation, 5 pages.

* cited by examiner

*Primary Examiner* — Andrea Olson
(74) *Attorney, Agent, or Firm* — Foley & Lardner LLP

(57) ABSTRACT

Provided is a method for collecting RNA contained in skin surface lipids (SSL). A method for preparing SSL-derived RNA. In this method, an aqueous solution containing RNA prepared from SSL of a subject is mixed with a water-soluble organic solvent, and the resulting mixture is allowed to contact with a solid phase material to separate RNA. By adjusting the concentration of the water-soluble organic solvent in the mixture, the yield of RNA improves.

5 Claims, No Drawings

METHOD FOR PREPARING RNA DERIVED FROM SKIN SURFACE LIPIDS

FIELD OF THE INVENTION

The present invention relates to a method for preparing RNA derived from skin surface lipids.

BACKGROUND OF THE INVENTION

Among various body tissues, the skin has drawn attention as a tissue from which biological samples can be collected in a less invasive manner because it is in contact with the external environment. In Patent Literature 1, it is described that skin surface lipids (SSL) contain RNA derived from a skin cell of a subject, and the RNA contained in SSL is useful as a sample for analyzing the living body. However, the amount of SSL which can be collected from a subject is not high nor the amount of RNA contained therein. Therefore, the amount of RNA which can be prepared from SSL of a single subject is low.

Examples of methods generally used for extracting nucleic acids such as RNA from biological samples include the phenol-chloroform method, acid guanidinium thiocyanate-phenol-chloroform extraction (AGPC) method, and their modified methods. Nucleic acid extraction reagents (such as TRIzol®) based on these principles have been commercially available. Patent Literature 2 describes a nucleic acid extraction method including dissolving a biological material to elute a nucleic acid contained therein, adding a water-soluble organic solvent to the solution containing the eluted nucleic acid to obtain a final concentration from 10 vol % to 60 vol % to prepare a lysate solution, and allowing the lysate solution to contact with a solid material, so that the nucleic acid is adsorbed to the solid material and collected.

(Patent Literature 1) WO 2018/008319
(Patent Literature 2) JP-A-2007-117084

SUMMARY OF THE INVENTION

The present invention provides a method for preparing RNA derived from skin surface lipids, including:

preparing an aqueous solution containing RNA from skin surface lipids of a subject;

mixing the aqueous solution with a water-soluble organic solvent to prepare a mixture; and allowing the mixture to contact with a solid phase material, so that the RNA in the mixture is adsorbed to the solid phase material, wherein the final concentration of the water-soluble organic solvent in the mixture before the contact with the solid phase material is 39 vol % or more and 50 vol % or less.

DETAILED DESCRIPTION OF THE INVENTION

All the Patent Literatures, Non-Patent Literature, and other publications cited herein are incorporated by reference in its entirety.

As used herein, the term "skin surface lipids; SSL" refers to a lipid-soluble fraction present on the skin surface and referred to as sebum in some cases. Generally, SSL mainly contains secretions secreted from the exocrine gland such as the sebaceous gland on the skin surface and is present on the skin surface in the form of a thin layer covering the skin surface.

As used herein, the term "skin" is a genetic term for regions including tissues on the body surface such as the epidermis, the dermis, the hair follicle, and the sweat glands, the sebaceous glands, and other glands, unless otherwise specified.

Improvement in the yield of RNA from skin surface lipids (SSL) is desired. The present invention relates to a method for collecting RNA contained in SSL.

The inventors of the present invention previously found that SSL contained RNA derived from a skin cell of a subject, which can be used for biological analyses, and submitted a patent application (Patent Literature 1). The present inventors further found that the yield of RNA prepared from SSL can be increased by adding a specific amount of water-soluble organic solvent to an aqueous solution containing RNA prepared from SSL, allowing the mixture to contact with a solid phase material, thus enabling RNA in the mixture to be efficiently adsorbed to the solid phase material. In the present invention, the inventors provide a method for preparing an SSL-derived RNA with which the RNA contained in SSL of a subject can be collected more efficiently.

According to the method of the present invention, the RNA contained in SSL can be collected with high yield. The present invention increases the number of detected RNA genes in analyses using RNA samples (such as genetic analysis and diagnosis), thus improving accuracy and efficiency of the analyses.

The subject in the method of the present invention may be any living organism which has SSL on the skin. Examples of the subject include mammals such as a human and a non-human mammal. Preferably the subject is a human. For example, the subject may be a human or a non-human mammal in need of or desiring an analysis of his/her or its own nucleic acid. Alternatively, the subject may be a human or a non-human mammal in need of or desiring an analysis of gene expression on the skin or analysis of the condition of the skin or regions other than the skin using a nucleic acid.

The SSL from the subject contains RNA expressed in a skin cell of the subject, preferably contains RNA expressed in any of the epidermis, sebaceous gland, hair follicle, sweat gland, and dermis of the subject, and more preferably, contains RNA expressed in any of the epidermis, sebaceous gland, hair follicle, and sweat gland of the subject (See Patent Literature 1). Therefore, the SSL-derived RNA prepared by the method of the present invention is preferably RNA derived from at least one region selected from the group consisting of the epidermis, sebaceous gland, hair follicle, sweat gland and dermis, and more preferably RNA derived from at least one region selected from the group consisting of the epidermis, sebaceous gland, hair follicle, and sweat gland.

The SSL-derived RNA prepared by the method of the present invention can include mRNA, tRNA, rRNA, small RNA (such as microRNA [miRNA], small interfering RNA [siRNA], Piwi-interacting RNA [piRNA]), long intergenic non-coding (linc) RNA, and the like. One or more of the RNA listed above can be contained in the SSL.

Examples of regions of the skin from which subject's SSL is collected include, but not limited to, the skin of any part of the body such as the head, face, neck, body trunk, and limbs, the skin having diseases such as atopy, acne, dryness, inflammation (redness), and tumors, and the skin having a wound.

Any means which have been used to collect or remove SSL from the skin can be used to collect SSL from the skin of the subject. An SSL absorbent material, an SSL adhesive material, or a tool for scraping SSL from the skin, as described below, can be preferably used. The SSL absorbent material or SSL adhesive material is not particularly limited as long as it is a material having an affinity for SSL, and examples thereof include polypropylene and pulp. More specific examples of the procedure for collecting SSL from the skin include a method for allowing SSL to be absorbed into a sheet-like material such as an oil-blotting paper or oil-blotting film; a method for adhering SSL to a glass plate, a tape, and the like; and a method for scraping SSL with a spatula, a scraper, and the like for collection. An SSL absorbent material which is pre-impregnated with a highly lipid soluble solvent may be used to improve the adsorption of SSL. On the other hand, it is not preferable that the SSL absorbent material contains a highly water-soluble solvent or water, because the adsorption of SSL is inhibited. The SSL absorbent material is preferably used in a dry state.

The SSL containing RNA collected from a subject may be stored until it is used for the RNA preparation as described below. The SSL containing RNA can be stored in a state as absorbed into the SSL absorbent material or adhered to the SSL adhesive material. The SSL containing RNA may be stored under a general storage condition of RNA (such as at −80° C.), but it can be stored under more mild conditions (WO2019/043040). For example, the temperature condition for storing the SSL containing RNA may be any temperature of 0° C. or lower, preferably −10° C. or lower, and more preferably −20° C. or lower. The storage period is not particularly limited, but is preferably 12 months or less, more preferably 6 months or less, and further more preferably 3 months or less.

The method for preparing an SSL-derived RNA of the present invention includes preparing an aqueous solution containing RNA from SSL of a subject, mixing the aqueous solution containing the RNA with a water-soluble organic solvent to prepare a mixture, and allowing the mixture to contact with a solid phase material. The intended SSL-derived RNA is collected from the solid phase material. In the present invention, examples of methods for preparing the aqueous solution containing RNA from SSL include the phenol-chloroform method which is a classical method for the RNA extraction using a mixture of acid phenol (such as water-saturated phenol) and chloroform, and its modified methods, such as the Phenol-chloroform-isoamyl alcohol (PCI) method, the acid guanidinium thiocyanate-phenol-chloroform extraction (AGPC) method, and a modified AGPC method in which guanidinium thiocyanate and phenol are pre-mixed. Preferably the modified AGPC method is used.

In the method of the present invention, the procedure for preparing an aqueous solution containing RNA from SSL is basically in accordance with the procedure of the RNA extraction from biological samples by the phenol-chloroform method. A specific example of the procedure is described below: to the SSL collected from a subject (or an SSL absorbent material or an SSL adhesive material containing the collected SSL), acid phenol is added and mixed, and then chloroform is added thereto and mixed to extract RNA from the SSL. Next the resulting mixture is centrifuged to be separated into an aqueous layer containing RNA (an upper layer) and a phenol-chloroform layer (a lower layer) (in some cases, a middle layer is also separated). The aqueous solution containing RNA is prepared from the SSL by collecting the aqueous layer.

Water saturated phenol may be used alone as the acid phenol used for the RNA extraction, and a reagent mixture containing phenol may also be used. For example, a reagent solution for the RNA extraction from biological samples which contains a commercially available RNA extraction reagent including guanidine thiocyanate (such as TRIzol® Reagent, QIAzol Lysis Reagent, ISOGEN) may be used as the reagent mixture containing phenol. It is preferable to use the commercially available reagent solution for the RNA extraction described above from the viewpoint of the efficiency of the RNA extraction from SSL. Thus, the modified AGPC method is preferably used for the RNA extraction. While chloroform is preferably used alone as the chloroform for the RNA extraction, a reagent mixture containing chloroform may also be used as long as a necessary amount of RNA is distributed to the aqueous layer.

As appropriate, the prepared aqueous solution containing RNA may be mixed with phenol and chloroform again and centrifuged to collect the aqueous layer. This procedure may be repeated 2 or more times. In addition, the prepared aqueous solution containing RNA may be mixed with chloroform again and centrifuged to collect the aqueous layer. This procedure may be repeated 2 or more times.

Next, the resulting aqueous solution containing RNA is mixed with a water-soluble organic solvent. Examples of the water-soluble organic solvent include alcohols such as primary alcohol, secondary alcohol, and tertiary alcohol, and among them, methanol, ethanol, isopropanol, n-propanol, and butanol can be preferably used. Butanol may be either with a linear or a branched structure. These alcohols can be used alone or 2 or more of them can be used in combination. Ethanol is more preferable from the viewpoint of reducing the environmental burden and toxicity to the workers. In the mixture of the aqueous solution containing RNA and the water-soluble organic solvent (hereinafter referred to as an RNA-solvent mixture), the final concentration of the water-soluble organic solvent (the concentration immediately before it is loaded into and in contact with a solid phase material as described below) may be 39 vol % or more and 50 vol % or less, preferably 40 vol % or more and 46 vol % or less, more preferably 41 vol % or more and 45.5 vol % or less, and further more preferably 42 vol % or more and 45 vol % or less. Adjusting the concentration of the water-soluble organic solvent in the mixture to the above range improves the yield of RNA from SSL. In the present invention, the vol % means a vol % at a temperature of 25° C. and a pressure of one atmosphere.

Next, RNA is collected from the RNA-solvent mixture. The collection of RNA can be performed in accordance with the nucleic acid separation method using a solid phase material. For example, the RNA-solvent mixture in which the final concentration of the water-soluble organic solvent has been adjusted as described above is allowed to contact with the solid phase material, so that the RNA in the mixture is adsorbed to the solid phase material. Next, impurities are washed away from the solid phase material as appropriate, and then the RNA is desorbed and collected from the solid phase material.

The solid phase material may be any nucleic acid adsorbent solid phase material, and examples thereof include a silica-based solid phase material. From the viewpoint of RNA adsorption, the solid phase material is preferably a solid phase material having a porous silica membrane. From the viewpoint of facilitating such operations as washing away impurities and eluting RNA, it is preferable that the solid phase material be in the form of a spin column, a pipette tube with a column, or a column cartridge which can be attached to a centrifuge tube or a pipette tube. Furthermore, from the viewpoint of the prevention of contamination and operational efficiency, the form of a spin column or a column cartridge which can be attached to a centrifuge tube is more preferable. In addition, in consideration of a relatively small amount of RNA collected from an individual subject through SSL, it is preferable that the solid phase material be in the form which can purify a small amount of RNA, such as a Miniprep Column. A commercially available RNA purification column can be used as the solid phase material, and examples thereof include RNeasy® Spin Column (QIAGEN) and NucleoSpin® RNA Column (Takara Bio Inc.).

As the washing liquid used for washing away impurities from the solid phase material, a solution and the like (such as an aqueous solution) containing at least one of the water-soluble organic solvent and water-soluble salt may be used. Alcohols can be used as the water-soluble organic solvent contained in the washing liquid. Examples of these alcohols include methanol, ethanol, isopropanol, n-propanol, butanol. Butanol can be either with a linear or a branched structure. Several of these alcohols can be used concurrently. It is preferable to use ethanol among them. The amount of the water-soluble organic solvent contained in the washing liquid may be any amount which allows for retaining the RNA on the solid phase material while washing away the impurities, and may be determined by those skilled in the art. The amount is preferably from 30 vol % to 100 vol % and more preferably from 35 vol % to 50 vol %. On the other hand, as the water-soluble salt contained in the washing liquid, a halide salt is preferable, and a chloride salt is especially preferable. As the water-soluble salt, a monovalent or bivalent cation salt is preferable, an alkali metal salt or an alkaline-earth metal salt is more preferable, a sodium salt and potassium salt are further more preferable, and a sodium salt is even more preferable. When the water-soluble salt is contained in the washing liquid, the concentration is preferably 10 mmol/L or more, and more preferably 20 mmol/L or more. On the other hand, the upper limit of the concentration is not especially specified as long as it does not impair the solubility of the impurities, but the concentration is preferably 1 mol/L or less, and more preferably 0.1 mol/L or less. Further more preferably, the water-soluble salt is a sodium chloride, and the concentration thereof in the washing liquid is preferably 20 mmol/L or more.

The desorption of the RNA from the solid phase material is performed preferably by flowing an eluate into the solid phase material to elute the RNA. Water, Tris-EDTA (TE) buffer, and the like can be used as the eluate used for the elution of the RNA. A washing liquid and eluate provided with a commercially available RNA purification column may be used as the washing liquid and eluate. The washing of the solid phase material and elution can be performed in accordance with the ordinary procedure. For example, when the solid phase material is loaded into the spin column, the RNA-solvent mixture is flown into the column, and the washing liquid is added to the column to which RNA is adsorbed, which is centrifuged to wash away impurities as well as the washing liquid. Then the eluate is added to the column, which is centrifuge to elute the RNA.

The solid phase material to which RNA is adsorbed may be treated with DNase as appropriate. The DNase treatment can improve the purity of the collected RNA by removing contaminating DNA. The DNase treatment is preferably performed between the washing of the solid phase material and the elution of RNA.

The RNA eluted from the solid phase material is the SSL-derived RNA of the subject and can be used for various analyses. For example, mRNA contained in the SSL-derived RNA can be used for the gene expression analysis, transcriptome analysis, and the like, after converted to cDNA using oligo (dT) primers. Alternatively, by testing for the presence or absence of target RNA in the SSL-derived RNA of the subject, it is possible to analyze functions of the subject, diagnose diseases and evaluate the efficacy of a drug administered to the subject.

As an exemplary embodiment of the present invention, the following substances, production methods, applications, methods, and the like are further disclosed herein. However, the present invention is not limited to these embodiments.

<1> A method for preparing RNA derived from skin surface lipids, the method comprising:

preparing an aqueous solution comprising RNA from skin surface lipids of a subject;

mixing the aqueous solution and a water-soluble organic solvent to prepare a mixture; and allowing the mixture to contact with a solid phase material, so that the RNA in the mixture is adsorbed to the solid phase material, wherein a final concentration of the water-soluble organic solvent in the mixture before the contact with the solid phase material is 39 vol % or more and 50 vol % or less.

<2> The method according to <1>, wherein the aqueous organic solvent is preferably alcohols, and more preferably at least one selected from the group consisting of methanol, ethanol, isopropanol, n-propanol, and butanol.

<3> The method according to <1> or <2>, wherein the preparation of the aqueous solution comprising the RNA is preferably performed in accordance with the phenol-chloroform method or modified methods thereof.

<4> The method according to any one of <1> to <3>, wherein the final concentration of the aqueous organic solvent in the mixture is preferably 40 vol % or more and 46 vol % or less, more preferably 41 vol % or more and 45.5 vol % or less, and further more preferably 42 vol % or more and 45 vol % or less.

<5> The method according to any one of <1> to <4>, wherein the solid phase material is preferably a silica-based solid phase material and more preferably a solid phase material having a porous silica membrane.

<6> The method according to <5>, wherein the solid phase material is preferably in the form of a spin column, a pipet tube with a column, or a column cartridge which can be attached to a centrifuge tube or a pipet tube.

<7> The method according to any one of <1> to <6> preferably further comprising collecting the RNA from the solid phase material.

<8> The method according to any one of <1> to <7> preferably further comprising washing the solid phase material to which the RNA has been adsorbed, and then eluting the RNA from the solid phase material.

<9> The method according to <8>, wherein a washing liquid for washing the solid phase material is preferably a solution comprising at least one selected from the group consisting of a water-soluble organic solvent and a water-soluble salt, wherein the water-soluble organic solvent is preferably alcohols, more preferably at least one selected from the group consisting of methanol, ethanol, isopropanol, n-propanol, and butanol, and the water-soluble salt is preferably a monovalent or bivalent cation salt, more preferably an alkali metal salt or an alkaline-earth metal salt, further more preferably a sodium salt and potassium salt, and also preferably chloride salt, and even more preferably a sodium chloride.

<10> The method according to <9>, wherein a concentration of the water-soluble organic solvent in the washing liquid is preferably from 30 vol % to 100 vol %, and more preferably from 35 vol % to 50 vol %.

<11> The method according to <9> or <10>, wherein a concentration of the water-soluble salt in the washing liquid is preferably 10 mmol/L or more and 1 mol/L or less, more preferably 10 mmol/L or more and 0.1 mol/L or less, further more preferably 20 mmol/L or more and 1 mol/L or less, and even more preferably 20 mmol/L or more and 0.1 mol/L or less.

<12> The method according to any one of <8> to <11>, wherein an eluate for eluting the RNA from the solid phase material is water or buffer.

<13> The method according to any one of <1> to <12>, wherein the skin surface lipids (SSL) are preferably comprised in an SSL absorbent material or an SSL adhesive material and more preferably comprised in an oil-blotting paper or an oil-blotting film.

EXAMPLES

The present invention will be described in more detail with reference to Examples but is not limited thereto.

Example 1 Separation of RNA from SSL—1

1) Four healthy males were selected as subjects. Sebum (SSL) was collected from the entire face of the subjects using an oil blotting film (5 cm×8 cm, made of polypropylene, 3M Japan Limited). The oil blotting film containing SSL was cut into appropriate sizes, all of which were placed in a 5-mL tube, and 1.425 mL of QIAzol® Lysis Reagent (QIAGEN) was added and mixed well to elute RNA from the sebum on the film. To 1.3 mL of the resulting solution, 260 μL of chloroform was added and mixed well, which was then centrifuged (at 15,000 rpm, 4° C. for 15 minutes) and 0.7 mL of the aqueous layer (upper layer) was collected as the aqueous solution containing RNA.

2) After mixing the aqueous solution containing RNA for four subjects obtained in 1) above, it was divided into 7 equal portions, and each was mixed with an equal amount of ethanol solution with various concentrations to prepare various mixtures with final ethanol concentrations in the range of from 35 vol % to 50 vol %. The total amount of the mixtures was passed through the silica-based column (RNeasy® spin column; QIAGEN). Then in accordance with the protocol provided with RNeasy®, the column was washed with a washing liquid included in the kit, followed by the elution of RNA with RNase-free Water and the eluate was collected. In the protocol provided with RNeasy®, the final ethanol concentration of the sample solution passed through the column is 35 vol %.

3) The RNA in the resulting eluate was quantified with Agilent 4200 TapeStation system (Agilent Technologies, Inc) using High Sensitivity RNA Screen Tape (Agilent Technologies, Inc) and High Sensitivity RNA ScreenTape Sample Buffer (Agilent Technologies, Inc).

4) Table 1 shows the amount of RNA collected from the mixture with various ethanol concentrations prepared in 2) above. The mixtures with final ethanol concentrations of 40 vol % or more improved RNA yields compared to the mixture with final ethanol concentration (35 vol %) as specified in the conventional protocol. The mixtures with final ethanol concentrations from 40 vol % to 45 vol % improved RNA yields more significantly.

TABLE 1

| Final ethanol concentration of mixture | RNA yield (ng) |
| --- | --- |
| 35.0 vol % | 1.41 |
| 37.5 vol % | 1.25 |
| 40.0 vol % | 2.14 |
| 42.5 vol % | 2.41 |
| 45.0 vol % | 2.35 |
| 47.5 vol % | 1.78 |
| 50.0 vol % | 1.68 |

Example 2 Separation of RNA from SSL—2

1) One healthy male was selected as a subject. An aqueous solution containing RNA was collected from SSL of the subject with the same procedure as in Example 1-1). The aqueous solution was divided into 3 equal portions, and each was mixed with an equal amount of ethanol solution with various concentrations to prepare mixtures with a final ethanol concentration of 35 vol %, 42.5 vol %, and 50 vol %. The total amount of the mixtures was passed through the silica-based column (NucleoSpin® RNA Column; Takara Bio Inc.). Then in accordance with the protocol provided with NucleoSpin®, the column was washed with a washing liquid provided with the kit, followed by eluting RNA with RNase-free Water and collecting the eluate. In the protocol provided with NucleoSpin®, the final ethanol concentration of the sample solution passed through the column is 35 vol %. The RNA in the eluate was quantified with the same procedure as Example 1-3).

2) Table 2 shows the amount of RNA collected from the mixtures with various ethanol concentrations prepared in 1) above. The mixtures with final ethanol concentrations of 42.5 vol % and 50 vol % significantly improved the RNA yield compared to the mixture with final ethanol concentration of 35 vol %.

TABLE 2

| Final ethanol concentration of mixture | RNA yield (ng) |
| --- | --- |
| 35.0 vol % | 17.1 |
| 42.5 vol % | 95.5 |
| 50.0 vol % | 60.5 |

Example 3 Comprehensive Analysis of Gene Expression Using Next-Generation Sequencer 1) Of the eluates containing RNA obtained in Example 1-2), those with final ethanol concentrations of 35 vol %, 42.5 vol %, and 50 vol % when applied to the column, and 4-fold diluted solutions of each eluate were used as samples for the gene expression analysis.

2) From each of the eluates containing RNA and diluted solutions thereof in 1) above, cDNA was synthesized by performing a reverse transcription at 42° C. for 90 min using SuperScript VILO cDNA Synthesis Kit (Life Technologies Japan Ltd.). Random primers provided with the kit were used as primers for the reverse transcription reaction. From the resulting cDNA, a library containing DNA derived from the 20802 gene was prepared by performing a multiplex PCR. The multiplex PCR was performed under the condition of [99° C., 2 min→(99° C., 15 sec→62° C., 16 min)×20 cycles→4° C., Hold] using Ion AmpliSeq Transcriptome Human Gene Expression Kit (Life Technologies Japan Ltd.). The obtained PCR product was purified with Ampure XP (Beckman Coulter Inc.), followed by performing reconstruction of the buffer, digestion of the primer sequence, adaptor ligation and purification, and amplification to prepare the library. The prepared library was loaded into Ion 540 Chip and sequenced using Ion S5/XL System (Life Technologies Japan Ltd.).

Table 3 shows the number of genes detected from the sequencing. The number of genes detected was 11,463 in the RNA eluate with a final ethanol concentration of 35 vol % when applied to the column, whereas the number of genes increased to 13,910 and 13,221 respectively, in eluates with final ethanol concentrations of 42.5 vol % and 50 vol % when applied to the column. This trend was more significant in the 4-fold diluted solutions of RNA eluates. Specifically, the number of genes detected in the diluted solution with a final ethanol concentration of 35 vol % when applied to the column was 8,898, whereas the number of genes detected in the diluted solutions with final ethanol concentrations of 42.5 vol % and 50 vol % when applied to the column significantly increased to 12,226 and 11,199, respectively. The results demonstrated that the RNA preparation method of the present invention is more beneficial for a sample with smaller collectable amount of RNA.

TABLE 3

| Final ethanol concentration when applied to column | Sample (Eluate containing RNA) | Number of detected genes |
| --- | --- | --- |
| 35.0 vol % | Undiluted eluate | 11,463 |
| 42.5 vol % | Undiluted eluate | 13,910 |
| 50.0 vol % | Undiluted eluate | 13,221 |
| 35.0 vol % | 4-fold diluted solution | 8,898 |
| 42.5 vol % | 4-fold diluted solution | 12,226 |
| 50.0 vol % | 4-fold diluted solution | 11,199 |

The invention claimed is:

1. A method for preparing RNA derived from skin surface lipids, the method comprising:

preparing an aqueous solution comprising RNA, wherein the RNA is separated from skin surface lipids obtained from a subject;

mixing the aqueous solution with ethanol to prepare a mixture; and allowing the mixture to contact with a silica-based solid phase material, so that the RNA in the mixture is adsorbed to the silica-based solid phase material, wherein a final concentration of the ethanol in the mixture before the contact with the solid phase material is 42 vol % or more and 45 vol % or less.

2. The method according to claim 1, wherein the aqueous solution comprising the RNA is prepared in accordance with the phenol-chloroform method or a modified method thereof, wherein the modified method is selected from the group consisting of a phenol-chloroform-isoamyl alcohol (PCI) method, an acid guanidinium thiocyanate-phenol-chloroform extraction (AGPC) method, and a modified AGPC method in which guanidinium thiocyanate and phenol are pre-mixed.

3. The method according to claim 1, wherein the silica-based solid phase material is a solid phase material having porous silica membrane.

4. The method according to claim 1, further comprising collecting the RNA from the silica-based solid phase material.

5. The method according to claim 1, wherein the skin surface lipids (SSL) are obtained from the subject using an SSL absorbent material or an SSL adhesive material.

\* \* \* \* \*